(12) United States Patent
Gagné

(10) Patent No.: US 9,588,098 B2
(45) Date of Patent: Mar. 7, 2017

(54) OPTICAL METHOD AND APPARATUS FOR IDENTIFYING WOOD SPECIES OF A RAW WOODEN LOG

(71) Applicant: Centre de recherche industrielle du Québec, Québec (CA)

(72) Inventor: Philippe Gagné, St-Nicolas (CA)

(73) Assignee: CENTRE DE RECHERCHE INDUSTRIELLE DU QUEBEC, Quebec (CA)

( * ) Notice: Subject to any disclaimer, the term of this patent is extended or adjusted under 35 U.S.C. 154(b) by 182 days.

(21) Appl. No.: 14/661,268

(22) Filed: Mar. 18, 2015

(65) Prior Publication Data

US 2016/0274022 A1    Sep. 22, 2016

(51) Int. Cl.
*G01N 33/46* (2006.01)
*G06T 7/00* (2006.01)

(52) U.S. Cl.
CPC ............... *G01N 33/46* (2013.01); *G06T 7/00* (2013.01); *G01N 2223/619* (2013.01); *G06T 2207/30161* (2013.01)

(58) Field of Classification Search
CPC .................. D01F 9/16; A61M 31/002; G06T 2207/30161; G01N 33/46; G01N 2223/619; G01N 21/8986
See application file for complete search history.

(56) References Cited

U.S. PATENT DOCUMENTS

| | | |
|---|---|---|
| 4,992,949 A | 2/1991 | Arden |
| 5,071,771 A | 12/1991 | Barbour et al. |
| 5,257,101 A | 10/1993 | Lee |
| 5,406,378 A * | 4/1995 | Jamroz ............. G01N 21/3563 356/432 |
| 5,544,757 A | 8/1996 | Geiger et al. |
| 5,761,070 A | 6/1998 | Conners et al. |
| 5,960,104 A | 9/1999 | Conners et al. |
| 6,072,890 A | 6/2000 | Savard et al. |
| 6,493,076 B1 | 12/2002 | Laitinen |

(Continued)

FOREIGN PATENT DOCUMENTS

CA    2302537 A1    9/2011

OTHER PUBLICATIONS

Ojala et al., A comparative study of texture measures with classification based on featured distributions, Pattern Recognition, 51-59, vol. 29, No. 1, Jan. 1, 1996.

(Continued)

*Primary Examiner* — Francis M Legasse, Jr.
(74) *Attorney, Agent, or Firm* — Jean-Claude Boudreau

(57) ABSTRACT

An optical apparatus and a method for identifying wood species of a raw wooden log involve directing light onto a representative portion of a peripheral surface of the wooden log, sensing light reflected on the illuminated representative log portion to generate reflection intensity image data including color image data, subdividing the reflection intensity image data into a plurality of image data regions each containing a preset number of image pixels, analyzing the image data regions to generate associated texture data, analyzing the color and texture data associated with each image data region to assign thereto a probable one of a plurality of species indications, and selecting a majority species indication for the inspected wooden log.

17 Claims, 10 Drawing Sheets

(56) References Cited

U.S. PATENT DOCUMENTS

| | | | |
|---|---|---|---|
| 7,406,190 | B2 | 7/2008 | Carman et al. |
| 7,426,422 | B2 | 9/2008 | Carman et al. |
| 8,193,481 | B2 | 6/2012 | Garneau et al. |
| 8,253,793 | B2 | 8/2012 | Hiraoka |
| 8,577,616 | B2 | 11/2013 | Dunlap |
| 2007/0133866 | A1* | 6/2007 | Chang ............... G06K 9/00 382/159 |
| 2012/0105626 | A1 | 5/2012 | Benoit et al. |
| 2014/0023280 | A1* | 1/2014 | Lin ............... G06F 17/30262 382/218 |

OTHER PUBLICATIONS

Tian et al., "Detection of Trimmed andOccluded Branches on HarvestedTree Stems using Texture Analysis", Journal of Forest Engineering, 65-78, vol. 8., No. 2, 1997.

Xie, "A Review of Recent Advances in Surface Defect Detection usingTexture analysis Techniques", Electronic Letters on Computer Vision and Image Analysis, 1-22, vol. 7, No. 3, 1998.

Metzler et al., Texture classification of gray-level images by multiscale cross co-occurrence matrices, 15th International Conference on Pattern Recognition, 549-552, vol. 2, Barcelona, Spain, Sep. 3, 2000.

Kauppinen, A Two Stage Defect Recognition Method for Parquet Slab Grading, 15th International Conference on Pattern Recognation, 803-806, vol. 4 Barcelona, Spain, Sep. 3, 2000.

Niskanen et al., Color and texture based wood inspection with non-supervised clustering, Scandinavian Conference on Image Analysis, 336-342, Bergen, Norway, Jun. 11, 2001.

Silven et al., Wood inspection with non-supervised clustering, Machine Vision and Applications, 275-285, vol. 13, Issue 5-6 Mar. 1, 2003.

Zhang et al., Local features and kernels for classification of texture and object categories: A comprehensive study International journal of computer vision, 213-238, vol. 73, No. 12, Sep. 1, 2006.

Fiel et al., Automated identification of tree species from images of the bark, leaves and needles, 16th Computer Vision Winter Workshop, Mitterberg, Austria, Feb. 2, 2011.

Doost et al. Texture Classification with Local Binary Pattern Based on Continues Wavelet Transformation International Journal of Advanced Research in Electrical, Electronics and Instrumentation Engineering 4651-4656 vol. 2, No. 10 Oct. 1, 2013.

* cited by examiner

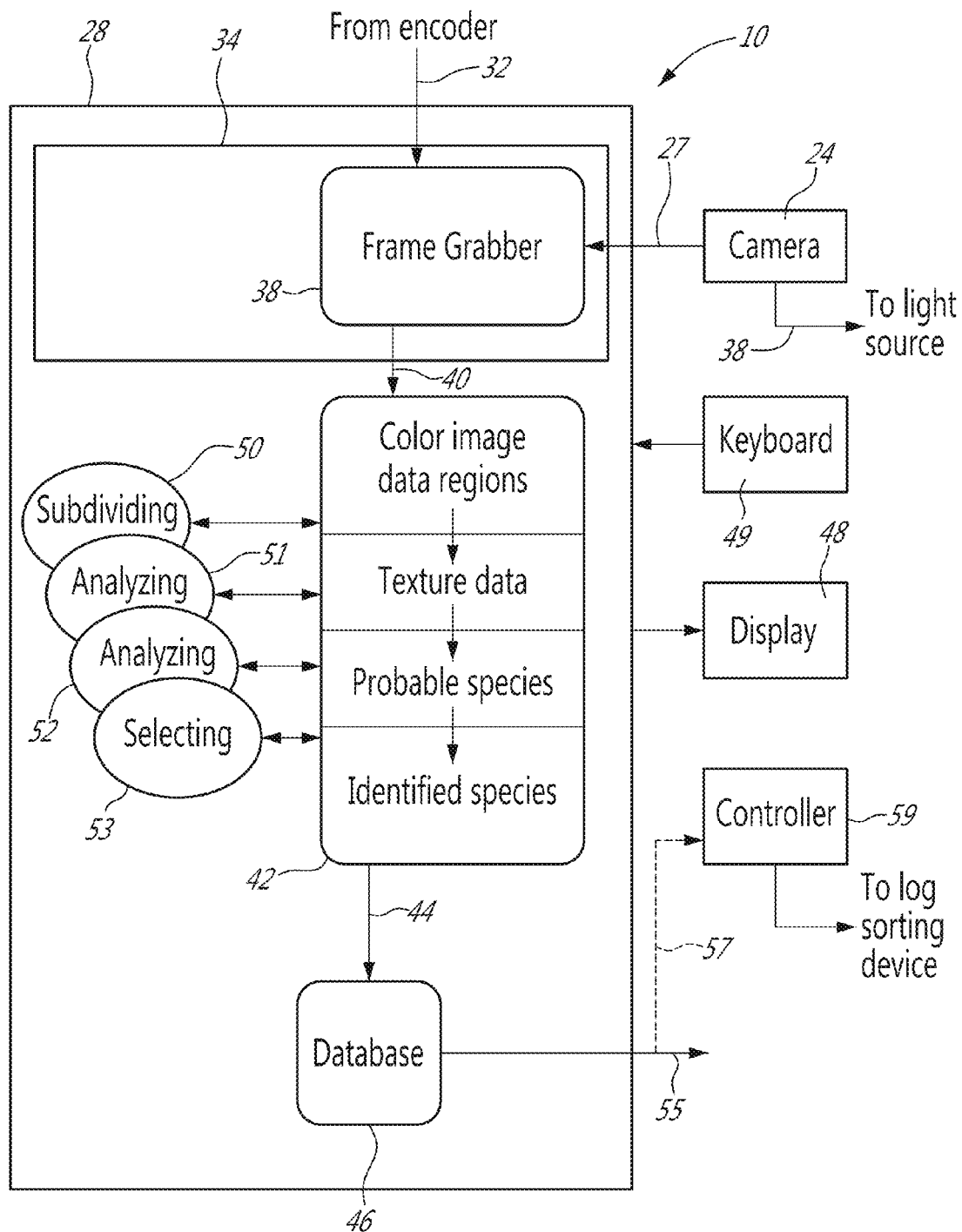

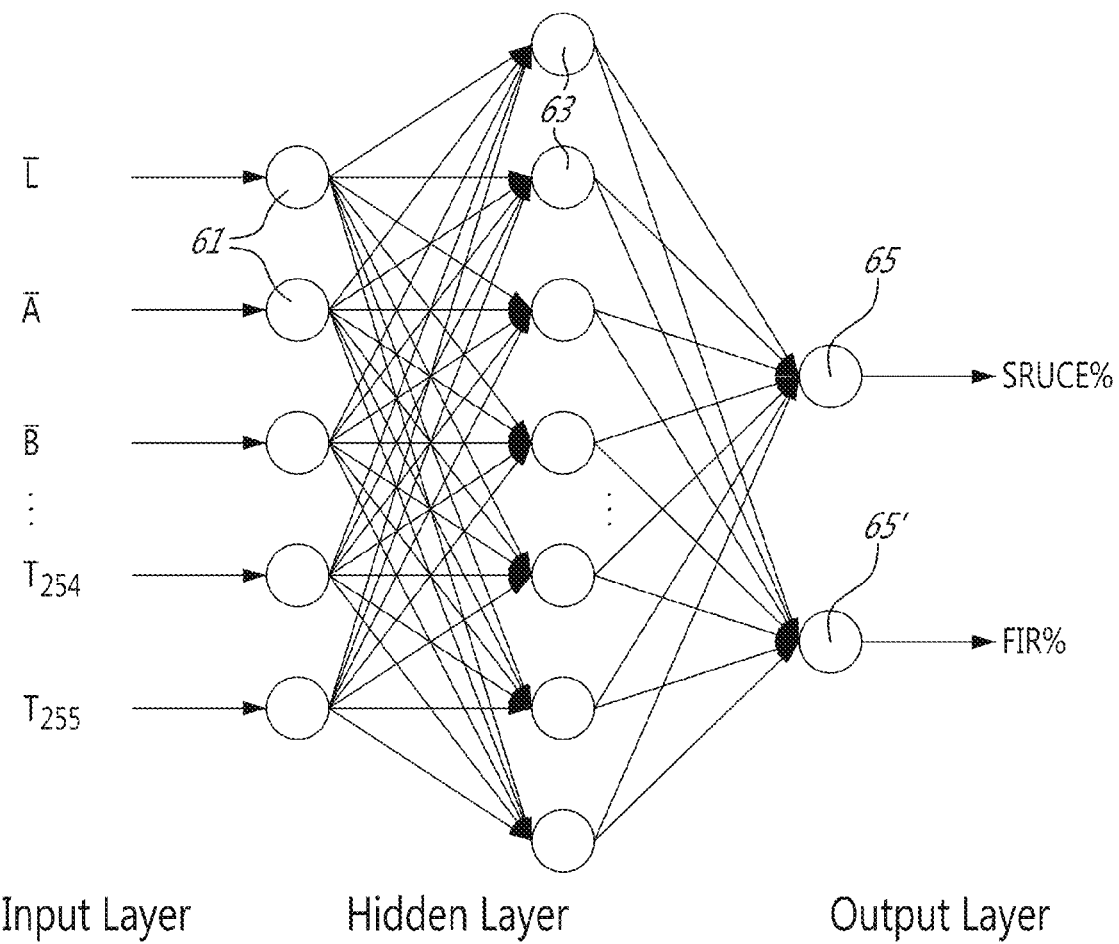
_FIG. 5_

Confusion Matrix

| | 1 | 2 | 3 | |
|---|---|---|---|---|
| 1 | 271<br>72.8% | 7<br>1.9% | 2<br>0.5% | 96.8%<br>3.2% |
| 2 | 33<br>8.9% | 50<br>13.4% | 9<br>2.4% | 54.3%<br>45.7% |
| 3 | 0<br>0.0% | 0<br>0.0% | 0<br>0.0% | 0<br>0.0% |
| | 89.1%<br>10.9% | 87.7%<br>12.3% | 0.0%<br>100% | 86.3%<br>13.7% |

Output Class (y-axis) / Target Class (x-axis)

FIG. 6

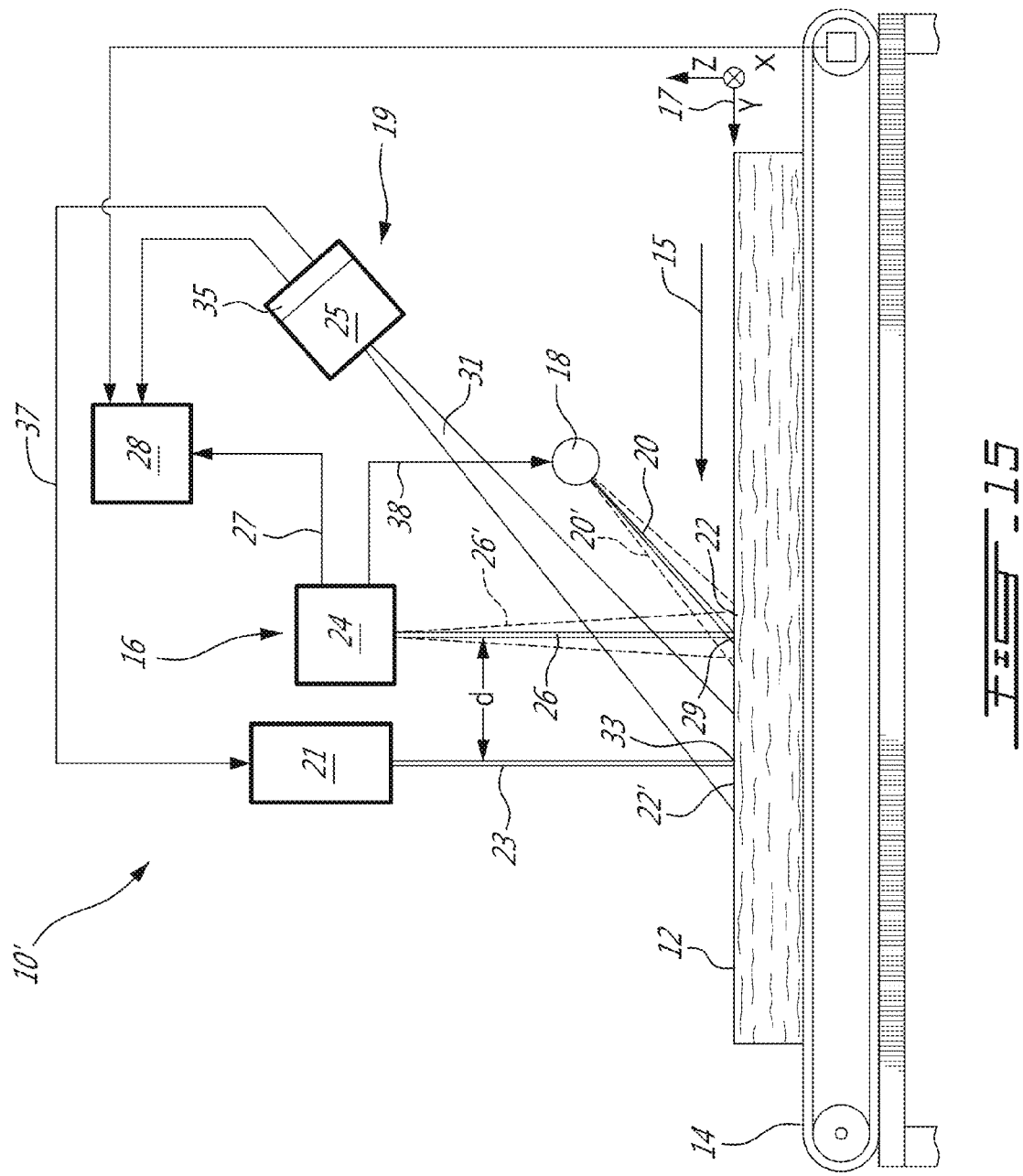

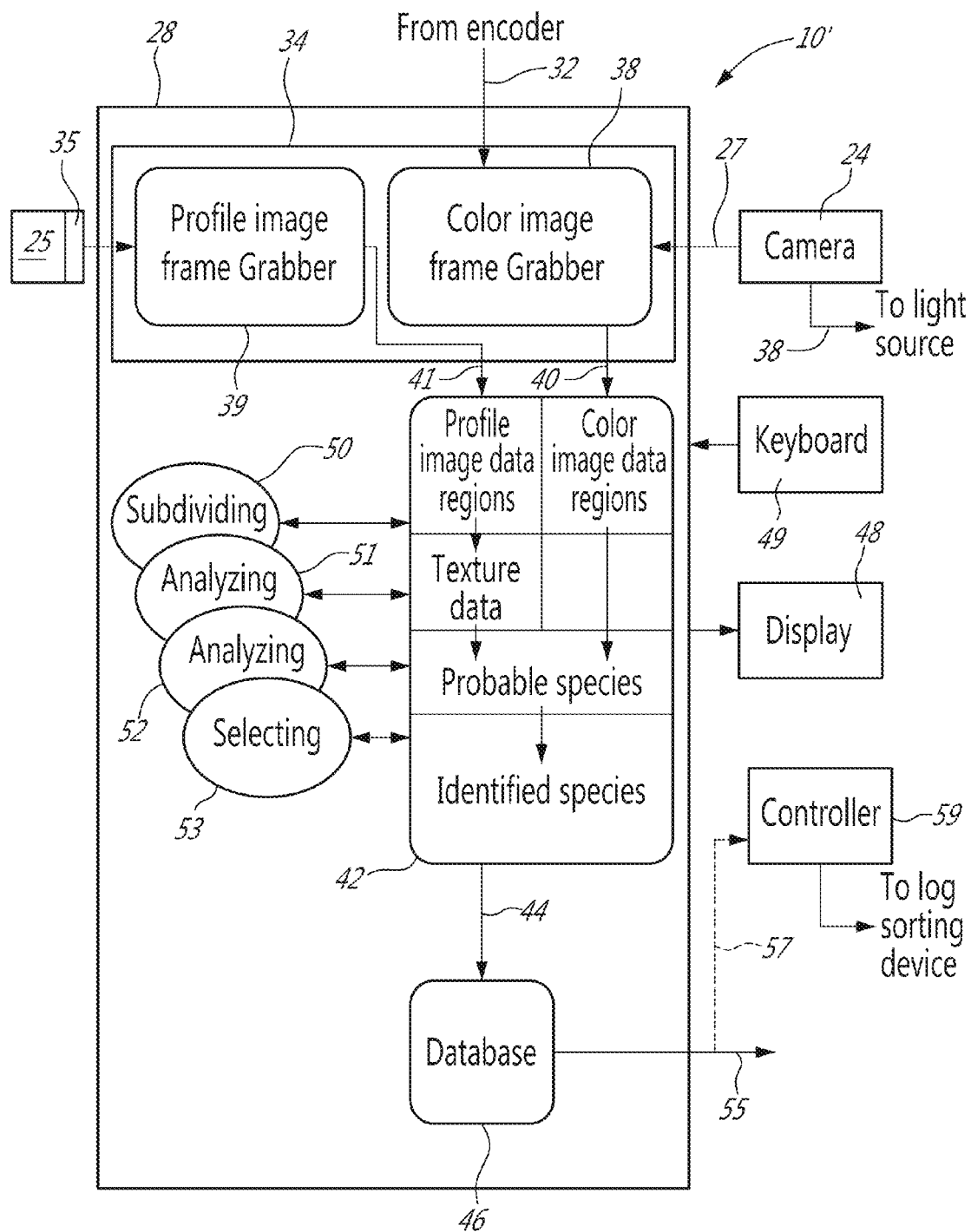

OPTICAL METHOD AND APPARATUS FOR IDENTIFYING WOOD SPECIES OF A RAW WOODEN LOG

TECHNICAL FIELD

The present invention pertains to the field of optical measurement techniques, and more particularly to optical method and apparatus for identifying wood species of wooden logs.

BACKGROUND OF THE INVENTION

In the lumber industry, it is generally known that sorting wooden logs upstream to the debarking line presents economical and operational advantages as compared to downstream sorting operations performed on the resulting wood products. Sorting by wood species can be carried out either as part of timber harvesting or in the lumberyard of the mill, and is generally performed by human operators through visual inspection of bark and/or cut-off surfaces of each piece of timber. However, manual inspection is time-consuming and generally exhibits a high misidentification rate. Although a high reliability of wood species identification may be obtained with microscopic inspection of wood fiber samples, such a laboratory technique cannot be practiced in a mill environment. In the past, some automated techniques aimed at wood species identification have been proposed. In U.S. Pat. No. 6,072,890, an indicator liquid is sprayed onto a fresh cut end of each piece of lumber to produce a characteristic reaction, e.g. based upon pH, and after a suitable interval of time, the coated ends of the lumber pieces are optically scanned for spectrographic analysis to identify the species of the piece of lumber, e.g. as between spruce and fir. Another technique disclosed in U.S. Pat. No. 5,071,771 is based on production of an ion mobility signature representing a wood sample, followed by comparing signatures to identify the species of the wood sample. However, such sample-based techniques do not provide wood species identification in real-time. In U.S. Published Patent application no. 2012/0105626, wood species identification is performed through fluorescence-based detection of pitch (resin) characteristics of wood surface exposed to a beam of UV radiation, causing pitch on or within the workpiece to emit visible light. Moreover, U.S. Pat. No. 5,406,378 discloses to perform wood species identification through irradiation of a wood sample with infra-red radiation intense enough to introduce microstructural modifications of the material surface, which can be detected measuring the intensity of the optical light reflected. However, such known optical techniques are not adapted to species identification for raw wooden logs, due to the presence of bark covering the wood fibers.

SUMMARY OF THE INVENTION

It is a main object of the present invention to provide optical method and apparatus for identifying wood species of raw wooden logs, through inspection of their peripheral surfaces.

According to the above-mentioned main object, from a broad aspect of the present invention, there is provided an optical method for identifying wood species of a raw wooden log, comprising the steps of: i) directing light onto at least a portion of a peripheral surface of said raw wooden log, the illuminated portion presenting light reflection characteristics being substantially representative of the log peripheral surface; ii) sensing light reflected on the illuminated representative log portion to generate reflection intensity image data associated with the log peripheral surface, the reflection intensity image data including color image data; iii) subdividing said reflection intensity image data into a plurality of image data regions each containing a preset number of image pixels; iv) analyzing each of said image data regions to generate associated texture data; v) analyzing the color and texture data associated with each of said image data regions to assign to each thereof a probable one of a plurality of species indications; and vi) selecting a majority one of said assigned species indications as said wood species identification of the raw wooden log.

According to the same main object, from another broad aspect, there is provided an optical apparatus for identifying wood species of a raw wooden log, comprising an optical sensor unit including a light source configured for directing light onto at least a portion of a peripheral surface of the raw wooden log, the illuminated portion presenting light reflection characteristics being substantially representative of said log peripheral surface, and an imaging sensor having a sensing field oriented to capture light reflected on the illuminated representative log portion and being configured to generate reflection intensity image data associated with the log peripheral surface, the reflection intensity image data including color image data. The apparatus further comprises data processing means programmed for subdividing the reflection intensity image data into a plurality of image data regions each containing a preset number of image pixels, analyzing each of said image data regions to generate associated texture data, analyzing the color and texture data associated with of each said image data regions to assign to each thereof a probable one of a plurality of species indications, and selecting a majority one of said assigned species indications as the wood species identification of the raw wooden log.

According to the same main object, from another broad aspect, there is provided an optical apparatus for identifying wood species of a raw wooden log, comprising a first optical sensor unit including a first light source configured for directing light onto at least a portion of a peripheral surface of the raw wooden log, the illuminated portion presenting light reflection characteristics being substantially representative of said log peripheral surface, and a first imaging sensor having a sensing field oriented to capture light reflected on the illuminated representative log portion and being configured to generate color image data. The apparatus further comprises a second optical sensor unit including a laser source configured for directing a linear-shaped laser beam onto the portion of the peripheral surface of the raw wooden log to form a reflected laser line onto said log peripheral surface, a second imaging sensor having a sensing field oriented to capture a two-dimensional image of the reflected laser line to generate corresponding two-dimensional image data, wherein said linear-shaped laser beam is directed at an angle with said sensing field, and first data processing means programmed for deriving profile-related image data from the corresponding two-dimensional image data. The apparatus further comprises second data processing means programmed for subdividing said color image data and profile-related image data into a plurality of image data regions each containing a preset number of image pixels, analyzing each of said profile-related image data regions to generate associated texture data, analyzing the color and texture data associated with each of said image data regions to assign to each thereof a probable one of a plurality of species indications, and selecting a majority one of said assigned species indications as the wood species identification of the raw wooden log.

The above summary of invention has outlined rather broadly the features of the present invention. Additional features and advantages of some embodiments illustrating the subject of the claims will be described hereinafter. Those skilled in the art will appreciate that they may readily use the description of the specific embodiments disclosed as a basis for modifying them or designing other equivalent structures or steps for carrying out the same purposes of the present invention. Those skilled in the art will also appreciate that such equivalent structures or steps do not depart from the scope of the present invention in its broadest form.

BRIEF DESCRIPTION OF THE DRAWINGS

Some embodiments of the present invention will now be described in detail with reference to the accompanying drawings in which:

FIG. 3 is a detailed block diagram of the basic embodiment of optical apparatus of FIG. 1, representing its main computer-based hardware and software components;

FIG. 5 is an example of a classification model based on a neural network structure;

FIG. 6 is a confusion matrix showing the results of a classification trial performed at a log processing plant;

FIGS. 7A to 14A are visual representations of probable species identifications for all regions within the log portions shown in the images of FIGS. 7 to 14;

FIG. 15 is a general block diagram of another embodiment of optical apparatus showing its main components; and FIG. 16 is a detailed block diagram of the basic embodiment of optical apparatus of FIG. 15, representing its main computer-based hardware and software components.

DETAILED DESCRIPTION

There are many wood species that could be identified using the method for which some embodiments are described below, such as spruce (black spruce, red spruce, white spruce, Norway spruce), balsam fir, pine (grey pine, scots pine, white pine, red pine, yellow pine), thuya (cedar), eastern hemlock, etc. For the sake of explanation, an example application for identifying spruce and balsam fir species is described below. The known appearance characteristics of these two species are presented in Table 1.

TABLE 1

| Species | Bark | Skin fiber | Heartwood | Sapwood |
|---|---|---|---|---|
| Black spruce | Thin and scaly; Dark gray-brown; | Dark olive | White | White |
| Red spruce | Thin and scaly; Pale reddish brown; Flakes on scales; | Pale olive | White | White |

TABLE 1-continued

| Species | Bark | Skin fiber | Heartwood | Sapwood |
|---|---|---|---|---|
| White spruce | Thin and scaly; Pale gray-brown; Few resin pockets (similar to those on balsam fir); | Silvery white | White | White |
| Norway spruce | Mix of reddish brown and smooth areas with dark; brown and scaly areas; Rigid scales; | | White | White |
| Balsam fir | Greyish and smooth when young; Brownish, irregular ridges with age; Resin pockets; | | White | White |

It can be appreciated that there are some potential identification keys for the species contemplated by the present example. For example, detection of spruce may be based on its brownish color and scaly texture of its bark, while detection of fir may be based on its greyish color and smooth texture of its bark. Moreover, the identification keys may consider the fact that various species of spruce exhibit significantly different appearance characteristics, e.g. that appearance depends on tree age, that resin pockets typical to fir may also be found on white spruce, and that bark of adult balsam fir tree takes a brownish color similar to that of bark of young black spruce tree. The optical detection performed by the proposed approach is essentially based on color and texture identification keys. Optionally, in order to better consider appearance variations due to tree age, an improved approach may be further based on an appropriate geometrical measurement related to tree age, such as a measurement of tree diameter made directly from the image data.

Figure 1:
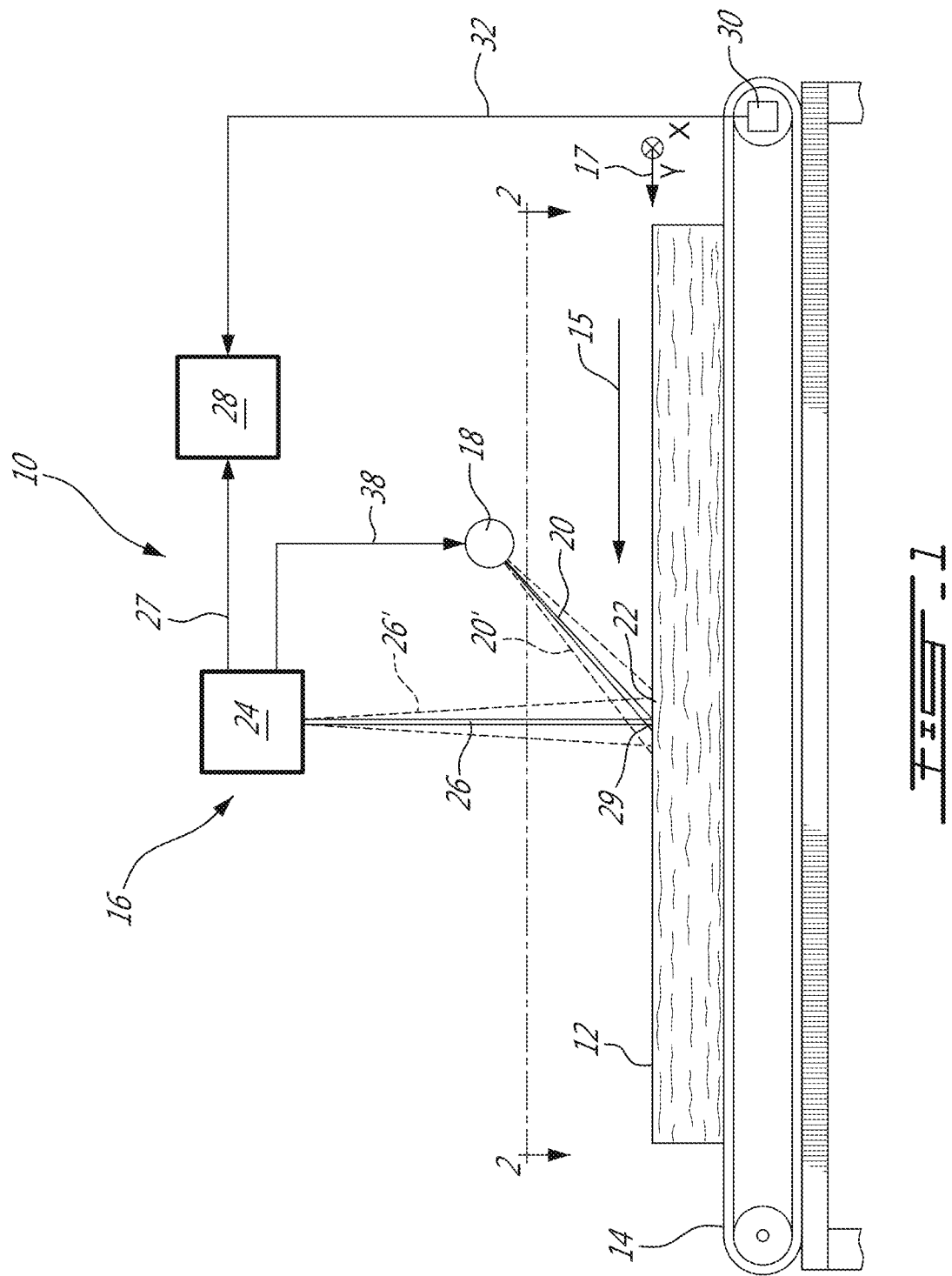
FIG. 1 is a general block diagram of a basic embodiment of an optical apparatus showing its main components while inspecting a wooden log transported on a conveyer represented in elevation view.
Figure 2:
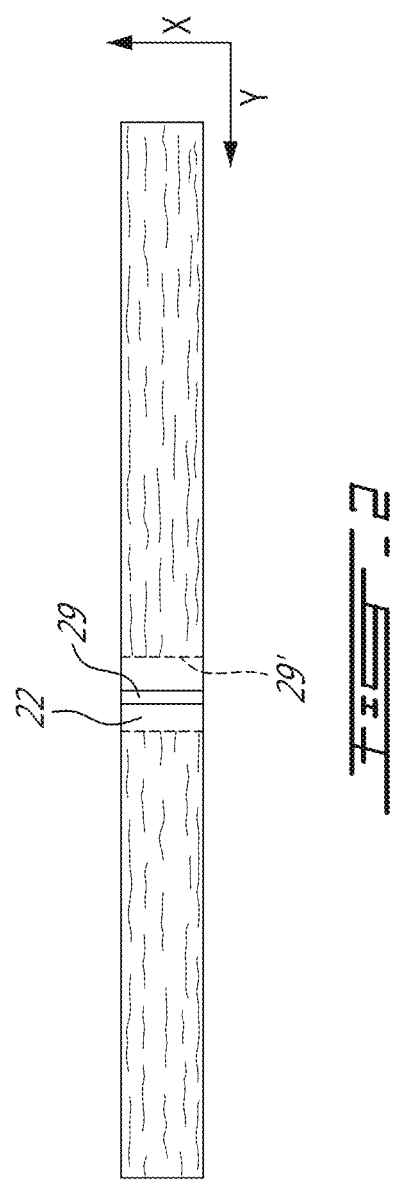
FIG. 2 is a plan view of the wooden log under inspection according to section lines 2-2 of FIG. 1.

Referring now to FIG. 1, there is shown a basic embodiment of apparatus generally designated at 10 for performing wood species identification of a raw wooden log 12 being transported on a conveyer 14 in the direction of arrow 15, which is parallel to Y axis of a reference system designated at 17, whose X axis extends perpendicularly to the transporting direction within the conveying plane as shown in FIG. 2. Although a flat belt conveyer 14 is shown in FIG. 1 for ease of illustration, a V-shaped belt conveyer restraining transverse movement of the log may also be used. The apparatus 10 includes an optical sensor unit generally designated at 16, which itself includes a light source 18 configured for directing a beam of light 20 onto at least a portion 22 of a peripheral surface of the raw wooden log 12. The extent of illuminated portion 22 is predetermined so that it presents light reflection characteristics substantially representative of the log peripheral surface, which is mainly constituted of bark. The optical sensor unit further includes an imaging sensor 24 having a sensing field 26 oriented to capture, within a scanning zone 29 of a sufficient depth of field, light reflected on the illuminated area 22, the imaging sensor 24 being configured to generate reflection intensity image data associated with the log peripheral surface, which data are sent via data line 27 to a computer 28, through a data acquisition unit as part of computer 28, which is configured for generating wood species identification of the raw wooden log 12 in a manner that will be described in detail below in view of FIG. 3. In an embodiment, the imaging sensor 24 is a digital color camera generating reflection intensity image data in the form of color image data.

In an embodiment, the imaging sensor may be a linear imaging sensor capable of generating image data in the form of a sequence of one-dimensional (along X axis) image signals as the inspected log 12 is transported lengthwise (along Y axis) on the conveyer 14 shown in FIG. 1, using a light source 18 capable of generating a narrow beam of light 20 so that the representative log portion surface 22 can be progressively illuminated as the log is moved. It can be seen from FIG. 1 in view of FIG. 22 that the sensing field 26 of the sensor unit 24 and the resulting scanning zone 29 can be accordingly narrow. A digital linear color camera such as model TVI Priimus 2048CQ from JAI Oy (Helsinki, Finland) may be used as imaging sensor 24 in that embodiment. In another embodiment, the imaging sensor may be a matrix imaging sensor capable of generating image data in the form of two-dimensional (X-Y axes) image signals, using a light source 18 such as a halogen lamp model Colortran (Leviton Mfg co, Melville N.Y.) capable of generating a wide beam of light 20' so that the representative log portion surface 22 is instantly illuminated during the sensor exposure time, with a shutter speed sufficiently high so that imaging quality is not adversely affected by the movement of the log. It can be seen from FIG. 1 in view of FIG. 2 that the sensing field 26' of the sensor unit 24 and the resulting scanning zone 29' can be accordingly wide. A digital matrix color camera such as model CV-M9GE, 1280×768 pixel, from JAI (San José, Calif., USA) may be used as imaging sensor 24 in that other embodiment. In both embodiments, the light source 18 may be operated in synchronization with the imaging sensor 24 through a control line 38. While the illuminated portion 22 is represented at a single location on the surface of the log according to the example shown in FIGS. 1 and 2, it should be understood that the illuminated portion 22 may be distributed at several locations of the log peripheral surface, so that the image data may be formed by several corresponding images captured at these locations, provided the resulting covered area 22 has an extent sufficient to present light reflection characteristics substantially representative of the log peripheral surface, as mentioned above.

Optionally, a moving camera can be used to better track the movement of the wooden log. In another embodiment, the conveyer 14 may be arranged to transport the wooden log transversely to its length while it is being scanned. As an alternative, the log 12 may be brought to a still position while one or more images are captured, using a matrix imaging sensor or a movable linear imaging sensor.

Although the computer 28 may conveniently be a general-purpose computer, an embedded processing unit such as based on a digital signal processor (DSP) can also be used to perform image frames generation. It should be noted that the present invention is not limited to the use of any particular computer, processor or digital camera as imaging sensor for performing the processing tasks of the invention. The term "computer", as that term is used herein, is intended to denote any machine capable of performing the calculations, or computations, necessary to perform the tasks of the invention, and is further intended to denote any machine that is capable of accepting a structured input and of processing the input in accordance with prescribed rules to produce an output. It should also be noted that the phrase "configured to" as used herein regarding electronic devices such as computer or digital camera, means that such devices are equipped with a combination of hardware and software for performing the tasks of the invention, as will be understood by those skilled in the art.

The computer 28 is programmed to perform image processing and analysis tasks, making use of computerized classification algorithms that take into consideration some identification keys in order to discriminate between the various wood species characterizing the scanned wooded logs in order to identify the species specific to each log with an acceptable probability.

Referring now to FIG. 3, the main computer-based hardware and software components of the basic embodiment of apparatus 10 will now be described in detail. The image acquisition unit 34 provided on the computer 28 is connected to the camera used as imaging sensor 24 to receive through line 27 the reflection intensity image data, in correspondence with physical sensed location on the inspected log surface. For so doing, the image acquisition unit 34 includes a frame grabber 38 programmed to integrate all necessary functions to associate reflection intensity image data with sensed location data for the scanned illuminated area 22, as well as all processing functions aiming at standardization of image specifications. As to the sensed location along Y axis on the inspected log surface, each log 12 may be either fed by conveyor 14 shown in FIG. 1 through the scanning zone of the optical apparatus 10 at a predetermined, substantially uniform speed, or at a varying speed or position/time profile in the transport direction. The speed or position/time profile measurement in accordance with actual speed conditions can be performed by providing means for measuring the actual speed or position/time profile of the moving log, such as a rotary encoder 30 shown in FIG. 1, or any appropriate non-contact detector (photocell array, laser velocimeter) disposed at a proper location along the log transport path, coupled to conveyer 14 and sending its output through line 32 to the data acquisition unit 34. Alternatively, the data acquisition unit may use a time synchronization approach, as disclosed in U.S. Pat. No. 8,193,481 issued to the same applicant, the entire content of which being incorporated herein by reference, wherein updating time data is used to perform sensor output data assembling with corresponding sensed location data related to log surface. Typically, the image resolution along X axis is intrinsic to pixel density of the sensor array (e.g. CMOS or CCD) provided on the digital camera 24, to any sub-pixelation algorithm used by the built-in processor of the camera, and further depends on the sensing field area as intersected by the log peripheral surface within the scanning zone. In an embodiment using a linear imaging sensor, the scanned log being displaced perpendicularly with respect to the sensor array of camera 24 to form a two-dimensional image, the resolution along Y axis is determined by the relative distance traversed by the log during the time gap between two successive image acquisition steps, which time gap substantially corresponds to the sensor exposure time. It is to be understood that image resolution along X axis can be different from resolution along Y axis. For image displaying and interpretation purposes, such resolution difference may be compensated by appropriate scaling. In an embodiment using a matrix imaging sensor, the image resolution along Y axis would be intrinsic to pixel density of the sensor array, to any sub-pixelation algorithm used, and would further depend on the sensing field area as intersected by the log peripheral surface within the scanning zone. Conveniently, a predetermined time gap between two successive image acquisition steps may be allocated to image processing and analysis tasks. In an embodiment, the raw images as taken by the digital camera are segmented to discriminate the relevant pixels associated with the wooden log surface from other pixels associated with the surrounding environment (e.g. conveyer surface), in order to limit the following image processing and analysis tasks only to relevant pixels. Prior to its operation, the camera 24 must be optically calibrated according to the supplier specifications to ensure image sensing accuracy, using any appropriate procedure involving color reference charts of predetermined image color intensity levels.

Figure 4A:
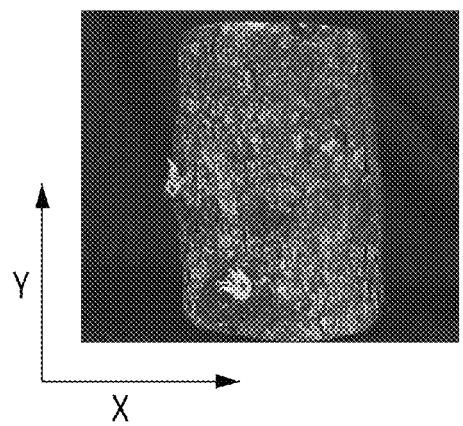
FIGS. 4A-4C are examples of reflected intensity images as generated by the imaging sensor of the apparatus of FIG. 1.
Figure 4B:
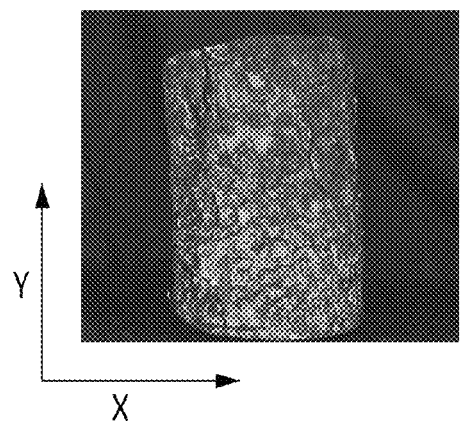
Figure 4C:
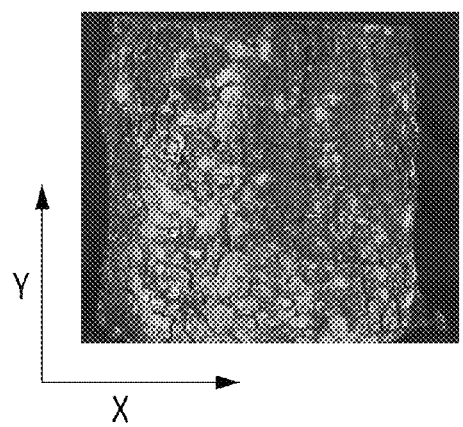
Figure 7:
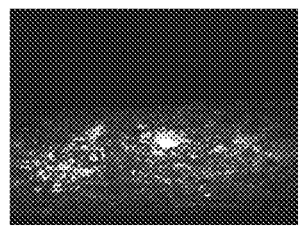
FIGS. 7 to 14 are reflected intensity images as captured on illuminated representative portions of 8 logs.
Figure 7A:
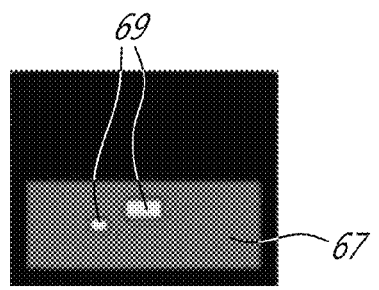
Figure 8:
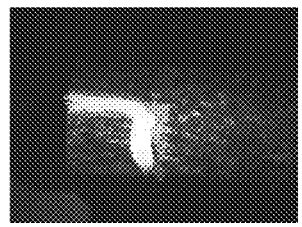
Figure 8A:
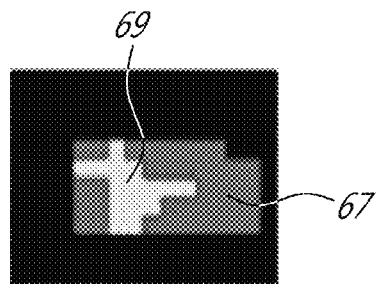
Figure 9:
Figure 9A:
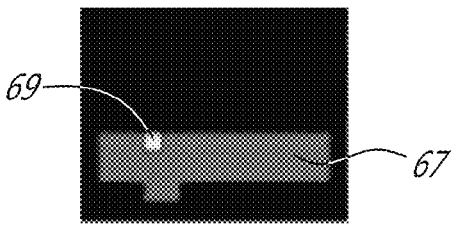
Figure 10:
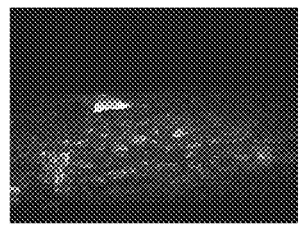
Figure 10A:
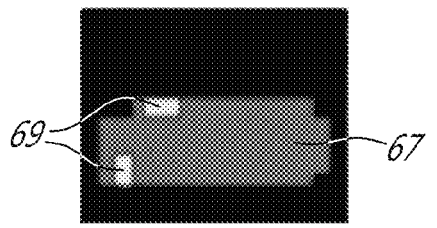
Figure 11:
Figure 11A:
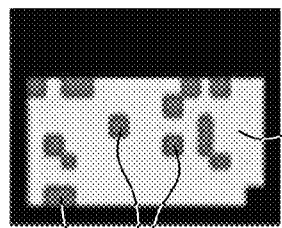
Figure 12:
Figure 12A:
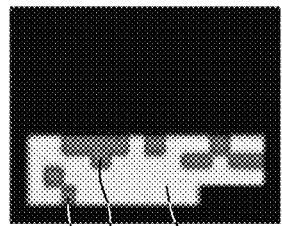
Figure 13:
Figure 13A:
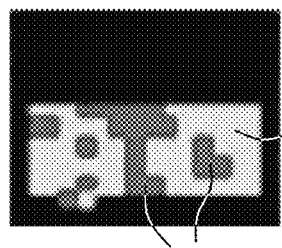
Figure 14:
Figure 14A:
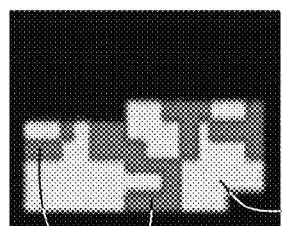

Exemplary reflected intensity images generated by the imaging sensor as formatted by the frame grabber 38 upon scanning of a log are shown in FIGS. 4A-4C, with respect to X and Y axes of the chosen reference system. Turning back to FIG. 3, the reflected intensity image data as generated by the frame grabber 38 are available at an output of the image acquisition unit 34 to be communicated through link 40 to the input of a data analyzing program module 42, whose ultimate function consists of identifying the species specific to each scanned log with an acceptable probability, to generate corresponding species indication data through link 44 to a database 46 and computer output 55. For so doing, the program module 42 may call for appropriate processing and analyzing subroutines identified at 50, 51, 52 and 53 in FIG. 3, which subroutines may be in the form of DLL files containing appropriate code for performing the desired functions, which will be described below in detail in view of examples. Although a DLL architecture may be conveniently used as a basis for the module 42 and other components of the computer program, any other architecture such as COM architecture may also be used for a same purpose. All data communication links described above may be implemented into a data communication network to provide data exchange between the camera 24, image acquisition unit 34, data analyzing program module 42 and database 78. Such a communication network can further be connected to a computer display 48 and data entry device such as keyboard 49 allowing an operator to make input parameter settings for the data analyzing program module 42. The species indication results may be shown to an operator via the display 48, in the form of images representing regions of the log surface portion to which probable species identifications have been assigned, as will be explained below in view of an example. Optionally, the species indication data are sent via line 57 to a controller 59 programmed to operate a log sorting device accordingly.

A basic task of the computer program consists in subdividing the reflection intensity image data into a plurality of image data regions each containing a preset number of image pixels, which task is performed by subroutine 50 shown in FIG. 3. For example, a 64×64 pixel region may be employed, totalizing 4096 pixels for each image data region. It is to be understood that the dimension of the image data regions may be set to other values, keeping in mind that a selection of a smaller dimension, which involves more pixel regions to be then processed and analysed, may increase the computing time, whereas a larger dimension could be detrimental to the reliability of species identification. As to the color information being part of the reflected intensity image data, it is basically derived from RGB color components currently generated by the digital color camera used as imaging sensor 24. The basic RGB color components exhibiting a certain level of correlation, a transformation into a known color space whose components are less correlated may be advantageously used in an embodiment of the present invention, in order to amplify its species discriminating capacity. As an example, the results of a comparison test for detection accuracy performed with known RGB, LAB, OHTA and HSV color spaces are shown in Table 2, involving a set of wooden logs whose respective species, either spruce or fir, have been previously identified through human visual inspection.

TABLE 2

| Color space components | Accurate detection (%) | |
|---|---|---|
| | Spruce | Fir |
| RGB (region mean) | 57.3% | 61.8% |
| RGB (region mean + std deviation) | 64.8% | 58.4% |
| Intensity (region mean + std deviation) | 59.4% | 57.3% |
| R and G (region mean + std deviation) | 62.6% | 58.8% |
| R and B (region mean + std deviation) | 64.6% | 59.7% |
| LAB (region mean) | 62.0% | 63.1% |
| OHTA (region mean) | 62.9% | 63.7% |
| HSV (region mean) | 64.0% | 59.9% |

It can be seen from Table 2 that for the present example, the mean component values associated with LAB and OHTA color spaces provide higher accuracy for both species detection as compared to corresponding values associated with other known color spaces.

As mentioned above, to complement the identification keys related to color, the optical detection performed by the proposed approach is also based on texture identification keys which can be taken into consideration through an appropriate image data analysis technique, to which each image data region is subjected through subroutine 51 shown in FIG. 3 so as to generate associated texture data. In an embodiment, the subroutine 51 is programmed for processing each image data region to generate associated texture data through a determination of local binary patterns (LBP) for each image data region, followed by calculation of a histogram of the obtained local binary patterns. A typical LBP analysis technique is described by Ojala et al. in <<A comparative study of texture measures with classification based on featured distributions>> Pattern Recognition, vol. 29, no 11, pp. 51-59, 1996, the entire content of which being incorporated herein by reference.

Basically, LBP image analysis for the purposes of the present method, consists of centrally applying a 3×3 pixel window over each pixel of the image region, comparing the target pixel intensity with respective values of the neighbouring pixels, for then assigning a <<1>> value if the neighbouring pixel intensity is larger than the target pixel intensity, and a <<0>> value otherwise. Hence, the sequence of binary values forms a 8 bits number, within a 0-256 range. Then, texture data can be expressed in the form of a histogram of the numbers obtained for all pixels of the image region. As an example, the results of a test for detection accuracy performed with LAB color space are compared in Table 3 with the result obtained with LAB and R-G color spaces in combination with texture information, involving the same set of wooden logs considered in the test presented above in view of Table 2.

TABLE 3

| Color space components/texture | Accurate detection (%) | |
|---|---|---|
| | Spruce | Fir |
| LAB mean + std deviation | 64.5% | 63.4% |
| Texture | 69.9% | 60.9% |
| LAB mean + std deviation and Texture | 75.3% | 68.7% |
| R − G mean + std deviation and Texture | 68.0% | 65.8% |

It can be seen from Table 3 that in the present example, that color data (LAB mean+std deviation) alone gives a good detection accuracy for fir, while texture data alone gives a better accuracy for spruce. However, it can be appreciated that the combination of color and texture data (LAB mean+std deviation and texture, R-G mean+std and texture) significantly improve detection accuracy for both species.

In a variant embodiment, the color image data may be expressed in terms of further statistical parameters, such as variance values. In another embodiment, a LBP filter can be used with or replaced by other digital filters, such as Laws or Gabor filters, which may react differently upon local image structures, so that a summing of these filter outputs may provide enhanced texture detection. Such multiple filtering technique is explained by Zhang et al. in <<Local features and kernels for classification of texture and object categories: A comprehensive study>> International journal of computer vision, vol. 73, no 12, pp. 213-238, 2007, the entire content of which being incorporated herein by reference.

While the use of a LBP filter provides ease of implementation as well as computing efficiency of that specific embodiment, other analysis techniques may be employed in other embodiments, such as a co-occurrence matrix technique, as explained by Metzler et al. in <<Texture classification of gray-level images by multiscale cross co-occurrence matrices>>, 15th International Conference on Pattern Recognition, Barcelona, Spain, 2000, and wavelet transformation technique, such as described by Doost et al. in <<Texture Classification with Local Binary Pattern Based on Continues Wavelet Transformation>>, International Journal of Advanced Research in Electrical, Electronics and Instrumentation Engineering, vol. 2, no 110, pp. 4651-4656, 2013, the entire contents of these papers being incorporated herein by reference.

Conveniently, the color image data and the texture data associated with each image data region is combined in the form a vector. The computer 28 is further programmed with subroutine 52 shown in FIG. 3 for analyzing the color and texture data associated with each image data region to assign to each thereof a probable one of a plurality of species indications. In an embodiment, the subroutine 52 makes use of a classification model previously trained with a set of raw wooden logs representative of the species indications. The classification consists of matching the vector associated with each image data region with corresponding vectors previously obtained as result of the training procedure, and making a decision on that basis. The classification model 110 may be built with any appropriate modeling platform such as a neural network, a support vector machine (SVM), a multivariate linear model, a static gain matrix or a fuzzy logic model. An example of classification model based on a feed-forward neural network structure is represented in FIG. 5, which model has and an input layer including 259 nodes 61 to receive values of the resulting vector in terms of mean color components and texture histogram values ($\overline{L}, \overline{A}, \overline{B}, T_0 \ldots T_{255}$), one hidden layer provided with an appropriate number (e.g. 10 or more) of nodes 63, and an output layer provided with nodes 65 and 65' that respectively generate indicating percentages of a first and a second wood species, namely spruce and fir in the specific example shown, from which a probable one (i.e. highest percentage) of these species indications can be obtained for the considered image region. In the instant example, the neural network model was trained using the fast training function "trainlm" of Matlab™, which function updates weight and bias to minimize errors using the Levenberg-Marquardt back-propagation training algorithm. The classification processing is carried out for the vectors associated with all image regions, resulting in a set of probable species indications.

The computer 28 is further programmed with subroutine 53 shown in FIG. 3 for selecting a majority one of the assigned species indications amongst all image regions, as the wood species identification of the raw wooden log. In an embodiment, the selection is based on a histogram built from the set of probable species indications for all image regions.

EXAMPLE 1

Table 3 presents species classification rates obtained with a neural network such as described above, from a laboratory trial involving validation and classification sets of 60 logs each, containing about 50% spruce and 50% fir, from each of which logs a set of color images were captured and subdivided in 64×64 pixels image regions for analysis.

TABLE 4

Accurate species detection (per region)

|  | Total | C1 - Spruce | C2 - Fir |
|---|---|---|---|
| Training set | 69.2% | 63.1% | 74.1% |
| Validation set | 66.4% | 66.1% | 66.7% |

It can be appreciated from Table 5 giving the obtained species classification rates for 24 logs representative of the validation set as grouped according to their predetermined species, that species detection errors are seldom made (logs nos. 22 and 44) so that species detection accuracy over 90% (10/11 for spruce, 12/13 for fir) is obtained for both spruce and fir classes as shown in Table 6.

TABLE 5

Accurate species detection (with grouping)

| Log ID | Class | Detection | C1 (%) | C2 (%) |
|---|---|---|---|---|
| 2 | 1 | 1 | 64.1% | 35.9% |
| 4 | 1 | 1 | 78.1% | 21.9% |
| 6 | 1 | 1 | 51.0% | 49.0% |
| 8 | 1 | 1 | 68.2% | 31.8% |
| 10 | 1 | 1 | 79.2% | 20.8% |
| 12 | 1 | 1 | 81.3% | 18.8% |
| 14 | 1 | 1 | 63.5% | 36.5% |
| 16 | 1 | 1 | 78.1% | 21.9% |
| 18 | 1 | 1 | 51.6% | 48.4% |
| 20 | 1 | 1 | 80.7% | 19.3% |
| 22 | 1 | 2 | 30.7% | 69.3% |
| 24 | 2 | 2 | 34.4% | 65.6% |
| 26 | 2 | 2 | 32.8% | 67.2% |
| 28 | 2 | 2 | 47.9% | 52.1% |
| 30 | 2 | 2 | 34.4% | 65.6% |
| 32 | 2 | 2 | 24.0% | 76.0% |
| 34 | 2 | 2 | 37.0% | 63.0% |
| 36 | 2 | 2 | 22.4% | 77.6% |
| 38 | 2 | 2 | 22.4% | 77.6% |
| 40 | 2 | 2 | 25.5% | 74.5% |
| 42 | 2 | 2 | 24.0% | 76.0% |
| 44 | 2 | 1 | 83.3% | 16.7% |
| 46 | 2 | 2 | 17.2% | 82.8% |
| 48 | 2 | 2 | 27.1% | 72.9% |

TABLE 6

Accurate species detection (per class)

|  | Total | Spruce | Fir |
|---|---|---|---|
| Validation set | 91.7% | 90.9% | 92.3% |

EXAMPLE 2

A classification trial was performed at a log processing plant, wherein a set of 176 spruce logs and 38 fir logs were visually identified by a skilled sorting operator, totalizing 214 logs, from which 1600 images were captured. A representative number of 112 images were first selected, from which 58 and 54 were respectively associated with spruce species and fir species, and then subdivided into 64×64 pixel regions. The resulting image data were used as a training set for species classification with a neural network such as described above. Amongst the remaining images, a representative number of 372 images were selected to constitute a validation set for the neural network, the resulting classification being illustrated (class 1: spruce; class 2: fir; claim 3; other) by the confusion matrix shown in FIG. 6, according to which 89.1% and 87.7% of the identified spruce species and fir species respectively, were accurately classified (target class) when compared with actual species (output class).

An example of species identification performed for a set of 8 raw wooden logs will now be presented in view of FIGS. 7 to 14 and FIGS. 7A to 14A, respectively showing reflected intensity images as captured on illuminated representative portions of the 8 logs, and corresponding visual representations of the probable species identifications for all regions within each log portion. In the visual representation shown in FIGS. 7A to 14A, each region to which a spruce species identification has been assigned appears depicted in dark gray at numeral 67, while each region to which a spruce species identification has been assigned appears in light gray at numeral 69. According to this example, it can be appreciated from FIGS. 7A to 10A, based on the histogram of species indications for the regions of each image, that spruce was the main emerging species indication assigned to the corresponding log portion images of FIGS. 7 to 10, whereas in view of FIGS. 11A to 14A, fir was the main emerging species indication assigned to the corresponding log portion images of FIGS. 11 to 14.

Another embodiment of optical apparatus according to the present invention, wherein the color image data is generated using an imaging sensor such as described above, while the texture data is obtained using a further imaging sensor, will now be described in reference to FIG. 15. The optical apparatus 10' according to the present embodiment is also capable of performing wood species identification of a raw wooden log 12 being transported on the conveyer 14 in the direction of arrow 15, which is parallel to Y axis of the reference system 17, whose X axis extends perpendicularly to the transporting direction within the conveying plane as shown in FIG. 15. The apparatus 10' includes a first optical sensor unit 16 of a same design as the one provided in the embodiment described above in view of FIG. 1, which itself includes a light source 18 configured for directing a beam of light 20 onto at least a portion 22 of a peripheral surface of the raw wooden log 12. Here again, the extent of illuminated portion 22 is predetermined so that it presents light reflection characteristics substantially representative of the log peripheral surface, which is mainly constituted of bark. The first optical sensor unit 16 further includes an imaging sensor 24 having a sensing field 26 oriented to capture, within a scanning zone 29 of a sufficient depth of field, light reflected on the illuminated area 22, the imaging sensor 24 being configured to generate color image data associated with the log peripheral surface, which data are sent via data line 27 to a computer 28, through a data acquisition unit as part of computer 28 which is configured for generating wood species identification of the raw wooden log 12 in a manner essentially identical as described above with reference to FIG. 3.

As explained above regarding the embodiment shown in FIG. 1, the imaging sensor 24 shown in FIG. 15 may be a linear imaging sensor capable of generating image data in the form of a sequence of one-dimensional (along X axis) image signals as the inspected log 12 is transported lengthwise (along Y axis) on the conveyer 14, using a light source 18 capable of generating a narrow beam of light 20 so that the representative log portion surface 22 can be progressively illuminated as the log is moved. As explained above regarding another embodiment, the imaging sensor may be a matrix imaging sensor capable of generating image data in the form of two-dimensional (X-Y axes) image signals, using a light source 18 capable of generating a wide beam of light 20' so that the representative log portion surface 22 is instantly illuminated during the sensor exposure time. It the log is caused to be moved during image capture, the shutter speed is set sufficiently high so that imaging quality is not adversely affected by the movement of the log. As explained above with reference to FIG. 1 in view of FIG. 2, the sensing field 26' of the sensor unit 24 and the resulting scanning zone 29' can be accordingly wide. In both of these embodiments, the light source 18 may be operated in synchronization with the imaging sensor 24 through control line 38.

The optical apparatus 10' further includes a second optical sensor unit 19 that itself includes a laser source 21 configured for directing a linear-shaped laser beam 23 onto the portion 22' of the peripheral surface of said raw wooden log to form a reflected laser line onto said log peripheral surface within a scanning zone 33, so that the representative log portion surface 22' can be progressively illuminated as the log is moved. In another embodiment, a self-scanning laser source may be used, especially when the log 12 is brought to a still position while profile imaging is performed. The second optical sensor unit 19 further includes a second imaging sensor 25 having a sensing field 31 oriented to capture a two-dimensional image of the reflected laser line to generate corresponding two-dimensional image data, wherein the linear-shaped laser beam 23 is directed at an angle with the sensing field 31. The second imaging sensor 25 is provided with a data processing means in the form of a processing module 35 programmed for deriving profile-related image data from the corresponding two-dimensional image data through a triangulation algorithm involving calculation of the center of gravity of the laser beam image, or any other appropriate algorithm, which profile-related data is associated with a reference axis (axis Z in reference system 17) orthogonal to a reference plane (plane X-Y in reference system 17) parallel to the transport direction. For example, the imaging sensor unit may use a same laser triangulation ranging approach as disclosed in U.S. Pat. No. 7,429,999 issued to the same applicant, the entire content of which document is incorporated herein by reference. The processing module 57 can be wholly or partially integrated into the digital camera 51, or be part of a computer system interfaced with the camera to receive and process raw image signals. The laser source 21 may be operated in synchronization with the imaging sensor 25 through a control line 37. In an embodiment, a CMOS digital 3D camera such as model C3-2350 from Automation Technology Gmbh (Germany) may be used as the second imaging sensor 25, along with a 630 nm compact laser from Osela Inc. (Pointe-Claire, Quebec, Canada).

The computer 28 is programmed to perform image processing and analysis tasks in a similar manner as performed by the embodiment described above with reference to FIGS. 1 and 3, making use of computerized classification algorithms that take into consideration some identification keys in order to discriminate between the various wood species characterizing the scanned wooded logs in order to identify the species specific to each log with an acceptable probability.

Referring now to FIG. 16 in view of FIG. 15, the main computer-based hardware and software components of the embodiment of apparatus 10' will now be described in detail. The image acquisition unit 34 provided on the computer 28 is connected to the camera used as imaging sensor 24 to receive through line 27 the reflection intensity image data, in correspondence with physical sensed location on the inspected log surface. For so doing, the image acquisition unit 34 includes a color image frame grabber 38 programmed to integrate all necessary functions to associate reflection intensity image data with sensed location data for the scanned illuminated area 22, as well as all processing functions aiming at standardization of image specifications. As to the sensed location along Y axis on the inspected log surface, each log 12 may be either fed by conveyor 14 shown in FIG. 15 through the scanning zone of the optical apparatus 10 at a predetermined, substantially uniform speed, or at a varying speed or position/time profile in the transport direction. The speed or position/time profile measurement in accordance with actual speed conditions can be performed by providing means for measuring the actual speed or position/time profile of the moving log, such as a rotary encoder 30 shown in FIG. 15, or any appropriate non-contact detector (photocell array, laser velocimeter) disposed at a proper location along the log transport path, coupled to conveyer 14 and sending its output through line 32 to the data acquisition unit 34. Alternatively, the data acquisition unit may use a time synchronization approach, as disclosed in U.S. Pat. No. 8,193,481 issued to the same applicant, the entire content of which document being incorporated herein by reference, wherein updating time data is used to perform sensor output data assembling with corresponding sensed location data related to log surface. It can be appreciated from FIG. 15 that the first and second optical sensor units 16, 19 in the embodiment shown are conveniently disposed one with respect to another so that their respective scanning zones 29, 33 are sufficiently spaced one with another along the transport direction to substantially prevent mutual scanning interference between first and second optical sensor units 16 and 19. In the example shown, the scanning plane associated with the sensing field 26 of the imaging sensor 24 and the scanning plane associated with the laser beam 23 are offset by a distance "d" in order to prevent illumination interference that would otherwise be caused by the laser beam 23 within the scanning zone 29 associated with first imaging sensor unit 24, and reciprocally by light beam 20 within the scanning zone 33 associated with the second imaging sensor 25. It can be appreciated that although simultaneous scanning of log portion surfaces 22, 22' may be carried out, the associated scanning planes being non coplanar due to the offset distance "d", these scanned surfaces are consequently not coplanar with respect to the reference axis (axis Y on the reference system 17) parallel to the transport direction. Therefore, there is a need for assembling respective output data generated by optical sensor units 16 and 19, with corresponding data representing location along the Y reference axis. For so doing, the image acquisition unit 34 further includes a profile-related image frame grabber 39 programmed to integrate all necessary functions to associate profile-related image data with sensed location data for the scanned illuminated area 22', as well as all processing functions aiming at standardization of image specifications. For so doing, as described above, the speed or position/time profile measurement in accordance with actual speed conditions can be used by the frame grabber 29 as received through line 32 to the data acquisition unit 34, or a time synchronization approach as disclosed in U.S. Pat. No. 8,193,481 issued to the same applicant may be employed. It is to be understood that any other appropriate data assembling technique can be used.

Prior to its operation, the digital camera 25 must be optically calibrated according to the supplier specifications to ensure image sensing accuracy, using any appropriate procedure involving reference charts of predetermined image intensity levels, such as a black-white-grey chart. Furthermore, the frame grabber 39 is programmed to apply spatial calibration of the measured 3D information in order to make accurate correspondence between the measured coordinates with respect to the camera reference system (i.e. in pixels), and the "world" coordinates (e.g. in mm) with respect to the physical reference system 17 of FIG. 16. For so doing, a calibration approach for use with a calibration target such as disclosed in U.S. Pat. No. 7,429,999 issued to the same applicant as of the present invention, the entire content of which document is incorporated herein by reference, or any other appropriate calibration technique, may be programmed in the frame grabber 39 including a proper interface for the operator to carry out calibration tasks. As a convention, a point (i, j) in a profile image is associated with a corresponding z profile coordinate along Z axis, wherein each line i of the image represents a y coordinate along Y axis which is parallel to transport direction indicated by arrow 15 in FIG. 15, and wherein each column j of that same image is associated with a sensor array column at a x coordinate along X axis.

As a result of applying spatial calibration, the measured centroid position coordinates (in pixel) for each column j of the camera sensor array is converted into "world" reference coordinates. Conveniently, the z coordinates are defined with respect to the central point of the calibration target that has been used in the calibration procedure that preceded operation of the system. Since initially, each coordinate j does not correspond to a constant, actual distance on the log surface with respect to x axis, image data as expressed with respect to the camera reference system are corrected by converting each j coordinate with respect to a physical reference, and each i within the same image data is associated to a constant physical distance in transverse direction along x axis. Conveniently, the results of spatial calibration may be generated in the form of image data complementary to profile image data and light intensity image data, so that three images associated with the scanned surface are basically created, the first representing z coordinate (profile) values of the detected centroids along Z axis, the second representing reflected light intensity values corresponding to the centroids, and the third representing x transverse coordinate values of the centroids along X axis. As mentioned above, a fourth image may be optionally created, representing laser line width at corresponding centroids. In an embodiment, the frame grabber is programmed to apply predetermined thresholds for assigning a preset value to pixels generated by the camera sensor array, which physically cannot correspond to a point of log surface, such as points associated with conveyer parts, and thrown or hanging bark fragments. The preset value, such as "0" or "9999", is chosen to be far from the valid pixel range, extending typically from a positive minimum value to a value between 100 and 1500 for example, to clearly discriminate valid pixels from invalid pixels. It is to be understood that the valid pixel range is influenced by many factors depending from the camera settings and calibration, as well as from the characteristics of the logs under inspection, such as wood species, diameters and lengths.

The color image data and the profiled-related image data as respectively generated by frame grabbers 38 and 39 are available at outputs of the image acquisition unit 34 to be communicated through links 40 and 41 to the input of a data analyzing program module 42, whose ultimate function consists of identifying the species specific to each scanned log with an acceptable probability, to generate corresponding species indication data through link 44 to a database 46 and computer output 55. For so doing, the program module 42 may call for appropriate processing and analyzing subroutines identified at 50, 51, 52 and 53 in FIG. 16, similar to the subroutines referred to above and bearing the same reference numerals in view of FIG. 3. All data communication links described above may be implemented into a data communication network to provide data exchange between cameras 24 and 25, image acquisition unit 34, data analyzing program module 42 and database 78. Such a communication network can further be connected to a computer display 48 and data entry device such as keyboard 49 allowing an operator to make input parameter settings for the data analyzing program module 42. The species indication results may be shown to an operator via a display 48, in the form of images representing regions of the log surface portion to which probable species identifications have been assigned. Optionally, the species indication data are sent via line 57 to a controller 59 programmed to operate a log sorting device accordingly.

In a similar manner as explained above regarding the embodiment shown in FIG. 3, a basic task of the computer program consists in subdividing the color image data (e.g. RGB, LAB, OHTA or HSV) and the profile-related image data into a plurality of image data regions each containing a preset number of image pixels (e.g. 64×64), which task is performed by subroutine 50 as shown in FIG. 16. As also explained above, to complement the identification keys related to color, the optical detection is also based on texture identification keys which can be taken into consideration through an appropriate texture extraction technique to which each region of resulting profile-related image data is subjected through subroutine 51 shown in FIG. 3 so as to generate associated texture data.

An exemplary implementation of processing and analyzing techniques capable of generating texture data will now be explained in detail. However, it is to be understood that any other appropriate processing and analyzing technique can be used by the person skilled in the art of image data processing for the same purpose.

As a first processing task, a segmentation subroutine is called for performing morphological segmentation of the resulting image data, in order to produce a binary mask image (referred to below as "mask_valid") wherein a valid pixel is assigned a value of "1", while any invalid pixel value is assigned a null value "0". For so doing, any of the intensity, laser line width, profile image or transverse coordinate image data can be used as starting data, since all of them have been assigned the same preset value for invalid pixels. The resulting binary image is then further processed by erosion using an appropriate structuring element of a few tens of lines by a few columns (e.g. matrix of 41×1 pixel) to move away from the edges inward, and outside pixels are cleaned to remove noise by applying an appropriate closing structural element of a few lines by a few columns (e.g. matrix of 5×5 pixel), to retain in the data only pixel values likely to be associated with a surface within the perimeter defined by the scanned log. Finally, the segmentation is completed by applying a structural element defining a threshold pixel area (e.g. 5000 pixel$^2$) to eliminate from the binary image very small blobs of pixels associated with noise, and preserve the larger blobs of valid pixels into the mask.

In practice, any of the intensity, laser line width, profile image or transverse coordinate image data may contain islands of invalid pixels that appear to be surrounded by valid pixels, which islands may be considered as noise deserving cleaning. Otherwise, these islands of invalid pixels could be wrongly associated with texture identification keys. Therefore, a second processing task aims at identifying the invalid pixel islands to then perform substitution by estimated valid pixel values through interpolation. For the purpose of this estimation, mean values derived from valid pixels surrounding invalid pixels of interest can be used. For so doing, an appropriate subroutine such as provided in libraries available on the marketplace such as "imfill" function of Matlab™ from Mathworks (Natick, Mass.), or "MblobReconstruct" function of MIL 9.0 from Matrox Electronics Systems (Dorval, Canada) can be used.

At that intermediary stage of processing, image data might not reflect the actual proportion of the corresponding surface region of the inspected log. As mentioned above, image deformation may be the result of higher image resolution along X axis as compared with image resolution along Y axis. From the resulting data, it is desirable to generate an image representing areas of the log surface respectively characterized by the detected species. As mentioned above, image data measurement is performed with respect to orthogonal reference axis X and Y that can be characterized by different resolution levels, which can be compensated by proper scaling of the resulting data, to provide a more realistic image displaying and to facilitate image interpretation by an operator. The scaling task may be performed by interpolation, whereby both scales along X and Y axis are modified according to a desired ratio, substantially without significant data alteration. For so doing, bicubic, nearest-neighbor or bilinear interpolation may be applied by calling an appropriate subroutine such as "imresize" function of Matlab™. Although image scaling is performed following the cleaning task in the present exemplary implementation, it could be performed either at an earlier or later stage of processing.

A next processing task aims at flattening the profile image data to compensate for the generally curved shape of the log surface, which could otherwise adversely affect the measurement accuracy of the texture identification keys. More specifically, flattening has the effect of assigning a substantially same weight to all surface areas covered by the sensing field of the second imaging sensor 25 shown in FIG. 15, regardless of their orientation within the scanning plane. The flattened profile image data (ima_Z_f) can be performed by applying to the scaled profile image data (ima_Z) a high-pass spatial frequency filter, conveniently obtained with subtraction of low-frequency data content, by calling an appropriate subroutine such as "imfilter" function of Matlab™ making use of a Gaussian-type convoluting kernel of 32 pixel dimension with 6 as standard deviation, according to the following command:

Ima_Z_f=imaZ−imfilter (ima_Z, fspecial ('gaussian', 32, 6))

In practice, the flattening task as performed on the scaled profile image may have a collateral effect of bringing out side pixels associated with high frequency transition out of the log perimeter. These outside pixels can be discarded for texture extraction purposes using the binary mask image "mask_valid" referred to above. As an alternative, the profile image data flattening can be performed by applying to the scaled profile image any appropriate curve-fitting algorithm known by the person skilled in the art of image data processing.

A next processing step aims at extracting the texture characterizing the profile image data. For so doing, a technique of edge detection can been applied, which consists of detecting vertical and horizontal edges of the profile image data with respect to the substantially longitudinal axis of the log to obtain texture data. According to the convention used hereinabove using reference system 17 shown in FIG. 15, horizontal and vertical edges may be respectively associated with axis Y and axis X. The detected horizontal and vertical edges are generated into the form of respective images (zhe and zve) on the basis of a Sobel convolution kernel, while reducing the dimension of the flattened image (ima_Z_f) by a predetermined factor (e.g. 0.5) to improve processing speed and reduce sensibility to noise, by calling an appropriate subroutine such as "resize" function of Matlab™ according to the following command:

$$zve = \text{resize}(ima\_Z\_f; 0.5) \circledast \begin{bmatrix} 1 & 0 & -1 \\ 2 & 0 & -2 \\ 1 & 0 & -1 \end{bmatrix}$$

$$zhe = \text{resize}(ima\_Z\_f; 0.5) \circledast \begin{bmatrix} 1 & 2 & 1 \\ 0 & 0 & 0 \\ -1 & -2 & -1 \end{bmatrix}$$

Finally, the intensity values of horizontal and vertical edges as generated may be separately summed to give the texture data associated with each image data region.

Conveniently, the color image data and the texture data associated with each image data region is combined in the form a vector. The computer 28 is further programmed with subroutine 52 shown in FIG. 16 for analyzing the color and texture data associated with each image data region to assign to each thereof a probable one of a plurality of species indications. As described above regarding the embodiment shown in FIG. 3, the subroutine 52 makes use of a classification model previously trained with a set of raw wooden logs representative of the species indications, which model may be a neural network, a support vector machine (SVM) a multivariate linear model, a static gain matrix or a fuzzy logic model. The computer 28 is further programmed with a subroutine 53 as shown in FIG. 16 for selecting a majority one of the assigned species indications amongst all image regions, as the wood species identification of the raw wooden log, the selection being conveniently based on a histogram built from the set of probable species indications for all image regions.

While the invention has been illustrated and described in detail below in connection with example embodiments, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

The invention claimed is:

1. An optical method for identifying wood species of a raw wooden log, comprising the steps of:
    i) directing light onto at least a portion of a peripheral surface of said raw wooden log, said illuminated portion presenting light reflection characteristics being substantially representative of said log peripheral surface;
    ii) sensing light reflected on the illuminated representative log portion to generate reflection intensity image data associated with said log peripheral surface, said reflection intensity image data including color image data;
    iii) subdividing said reflection intensity image data into a plurality of image data regions each containing a preset number of image pixels;
    iv) analyzing each of said image data regions to generate associated texture data;
    v) analyzing the color and texture data associated with each of said image data regions to assign to each thereof a probable one of a plurality of species indications; and
    vi) selecting a majority one of said assigned species indications as said wood species identification of the raw wooden log.

2. The method according to claim 1, wherein said wood species identification is one of species of spruce and fir.

3. The method according to claim 1, wherein said analyzing step v) is performed with a classification model previously trained with a set of raw wooden logs representative of said plurality of species indications.

4. The method according to claim 2, wherein said classification model is a neural network model.

5. The method according to claim 1, wherein color image data is defined in one of a LAB color space and OHTA color space.

6. The method according to claim 5, wherein said color image data is expressed as values selected from the group consisting of mean values, standard deviation values, variance values, or any combination thereof.

7. The method according to claim 1, wherein said analyzing step iv) includes:
    a) determining local binary patterns for each of said image data regions;
    b) calculating a histogram of said local binary patterns to generate said associated texture data.

8. The method according to claim 1, wherein said selecting step vi) includes calculating a histogram of said assigned species indications.

9. An optical apparatus for identifying wood species of a raw wooden log, comprising:
    an optical sensor unit including:
        a light source configured for directing light onto at least a portion of a peripheral surface of said raw wooden log, said illuminated portion presenting light reflection characteristics being substantially representative of said log peripheral surface; and
        an imaging sensor having a sensing field oriented to capture light reflected on the illuminated representative log portion and being configured to generate reflection intensity image data associated with said log peripheral surface, said reflection intensity image data including color image data; and
    data processing means programmed for subdividing said reflection intensity image data into a plurality of image data regions each containing a preset number of image pixels, analyzing each of said image data regions to generate associated texture data, analyzing the color and texture data associated with each of said image data regions to assign to each thereof a probable one of a plurality of species indications, and selecting a majority one of said assigned species indications as said wood species identification of the raw wooden log.

10. The apparatus according to claim 9, wherein said wood species identification is one of species of spruce and fir.

11. The apparatus according to claim 9, wherein said data processing means is programmed for analyzing the color and texture data with a classification model previously trained with a set of raw wooden logs representative of said plurality of species indications.

12. The apparatus according to claim 11, wherein said classification model is a neural network model.

13. The apparatus according to claim 9, wherein color image data is defined in one of a LAB color space and OHTA color space.

14. The apparatus according to claim 13, wherein said color image data is expressed as values selected from the group consisting of mean values, standard deviation values, variance values, or any combination thereof.

15. The apparatus according to claim 9, wherein said data processing means is programmed for processing each of said image data regions to generate associated texture data through a determination of local binary patterns for each of said image data regions, followed by calculation of a histogram of said local binary patterns.

16. The apparatus according to claim 9, wherein said data processing means is programmed for selecting a majority one of said assigned species indications as said wood species identification of the raw wooden log through a calculation of a histogram of said assigned species indications.

17. An optical apparatus for identifying wood species of a raw wooden log, comprising:

a first optical sensor unit including:
  a first light source configured for directing light onto at least a portion of a peripheral surface of said raw wooden log, said illuminated portion presenting light reflection characteristics being substantially representative of said log peripheral surface; and
  a first imaging sensor having a sensing field oriented to capture light reflected on the illuminated representative log portion and being configured to generate color image data;
a second optical sensor unit including:
  a laser source configured for directing a linear-shaped laser beam onto the portion of the peripheral surface of said raw wooden log to form a reflected laser line onto said log peripheral surface;
  a second imaging sensor having a sensing field oriented to capture a two-dimensional image of said reflected laser line to generate corresponding two-dimensional image data, wherein said linear-shaped laser beam is directed at an angle with said sensing field; and
  first data processing means programmed for deriving profile-related image data from said corresponding two-dimensional image data; and
second data processing means programmed for subdividing said color image data and profile-related image data into a plurality of image data regions each containing a preset number of image pixels, analyzing each of said profile-related image data regions to generate associated texture data, analyzing the color and texture data associated with each of said image data regions to assign to each thereof a probable one of a plurality of species indications, and selecting a majority one of said assigned species indications as said wood species identification of the raw wooden log.

* * * * *